(12) United States Patent
Schendel

(10) Patent No.: US 7,931,469 B1
(45) Date of Patent: Apr. 26, 2011

(54) ORTHODONTIC ANCHOR

(76) Inventor: Stephen A. Schendel, Menlo Park, CA (US)

( * ) Notice: Subject to any disclaimer, the term of this patent is extended or adjusted under 35 U.S.C. 154(b) by 75 days.

(21) Appl. No.: 12/386,515

(22) Filed: Apr. 20, 2009

Related U.S. Application Data

(62) Division of application No. 11/784,566, filed on Apr. 9, 2007, now abandoned.

(51) Int. Cl.
*A61C 7/00* (2006.01)

(52) U.S. Cl. ......... 433/18; 433/173; 24/573.09; 24/482; 24/DIG. 31

(58) Field of Classification Search ............... 433/8, 10, 433/13, 14, 18, 19, 24, 172–176, 225; 606/70, 606/280, 71, 74, 103, 258, 259, 260, 263, 606/285, 302; 24/573.09, 17 B, 482, DIG. 31, 24/339; 63/3.1, 14.7, 22; 403/286, 293, 403/316, 317; 439/369, 370
See application file for complete search history.

(56) References Cited

U.S. PATENT DOCUMENTS

| | | | | |
|---|---|---|---|---|
| 481,262 A * | 8/1892 | Heard et al. | ................ | 403/286 |
| 1,436,882 A * | 11/1922 | Knepper | ................ | 285/319 |
| 3,475,716 A * | 10/1969 | Laig | ................ | 439/369 |
| 3,741,205 A * | 6/1973 | Markolf et al. | ................ | 606/291 |
| 3,881,753 A * | 5/1975 | Bochory | ................ | 285/82 |
| 3,953,060 A * | 4/1976 | Eross | ................ | 285/272 |
| 3,957,380 A * | 5/1976 | DeGrazia | ................ | 403/14 |
| 4,112,988 A * | 9/1978 | Nelson | ................ | 81/456 |
| 4,183,603 A * | 1/1980 | Donarummo | ................ | 439/369 |
| 4,311,463 A * | 1/1982 | Glattly | ................ | 433/18 |
| 4,543,692 A * | 10/1985 | Ode et al. | ................ | 24/616 |
| 4,690,476 A * | 9/1987 | Morgenrath | ................ | 439/502 |
| 4,773,874 A * | 9/1988 | Kopeski, Jr. | ................ | 439/369 |
| 4,898,542 A * | 2/1990 | Jones, Jr. | ................ | 439/371 |
| 4,913,468 A * | 4/1990 | Rattmann | ................ | 285/82 |
| 4,957,450 A * | 9/1990 | Pioszak | ................ | 439/369 |
| 5,052,930 A * | 10/1991 | Lodde et al. | ................ | 433/173 |
| 5,309,609 A * | 5/1994 | Janiszewski et al. | ........... | 24/339 |
| 5,385,583 A * | 1/1995 | Cotrel | ................ | 606/270 |
| 5,573,420 A * | 11/1996 | Grosswendt | ................ | 439/371 |
| 5,634,926 A * | 6/1997 | Jobe | ................ | 606/281 |
| 5,678,282 A * | 10/1997 | Stewart | ................ | 24/68 J |
| 5,733,138 A * | 3/1998 | Kramer | ................ | 439/369 |
| 5,782,236 A * | 7/1998 | Ess | ................ | 128/207.17 |
| 5,782,631 A * | 7/1998 | Kesling et al. | ................ | 433/14 |
| 6,076,424 A * | 6/2000 | McMurtrey et al. | ........... | 74/544 |
| 6,089,862 A * | 7/2000 | Schutz | ................ | 433/18 |
| 6,168,429 B1 * | 1/2001 | Brown | ................ | 433/11 |
| 6,440,135 B2 * | 8/2002 | Orbay et al. | ................ | 606/286 |
| 6,896,514 B2 * | 5/2005 | DeVincenzo | ................ | 433/24 |
| 7,281,923 B1 * | 10/2007 | DeVincenzo et al. | .......... | 433/18 |
| 7,637,741 B2 * | 12/2009 | Devincenzo et al. | ......... | 433/174 |
| 2002/0071718 A1* | 6/2002 | Marty et al. | ................ | 403/293 |
| 2002/0150856 A1* | 10/2002 | Payton | ................ | 433/8 |
| 2003/0104335 A1* | 6/2003 | Chung | ................ | 433/18 |
| 2004/0147931 A1* | 7/2004 | De Clerck | ................ | 606/70 |
| 2004/0166461 A1* | 8/2004 | Devincenzo | ................ | 433/18 |
| 2004/0247381 A1* | 12/2004 | Bruckner | ................ | 403/286 |
| 2005/0142513 A1* | 6/2005 | Hotta | ................ | 433/18 |
| 2005/0147938 A1* | 7/2005 | Devincenzo et al. | ........... | 433/18 |
| 2005/0266369 A1* | 12/2005 | Scommegna et al. | ........... | 433/15 |

* cited by examiner

*Primary Examiner* — Todd E Manahan
*Assistant Examiner* — Michael R Ballinger
(74) *Attorney, Agent, or Firm* — Rodgers & Rodgers

(57) ABSTRACT

An orthodontic anchor having a stem with a connecting portion and an emerging portion secured respectively to the ends thereof. The connecting portion is connected to bone by screws disposed in angled apertures and a cap envelops the emerging portion. A first transverse rib secured to the lower edge of the cap and a second transverse rib secured to the anchor between the connecting and emerging portions and an elastic band enveloping both transverse ribs.

3 Claims, 2 Drawing Sheets

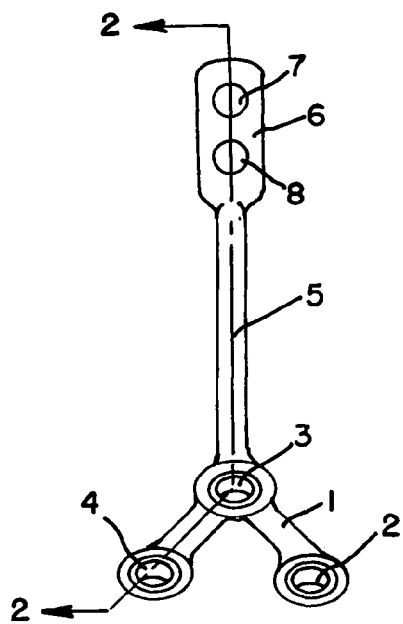
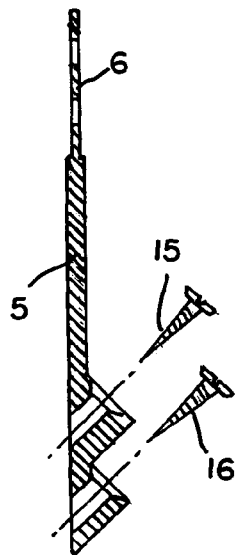
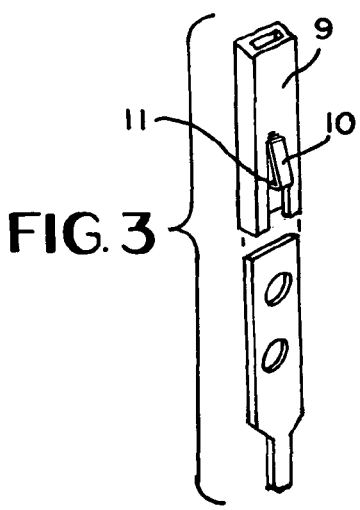
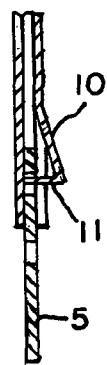
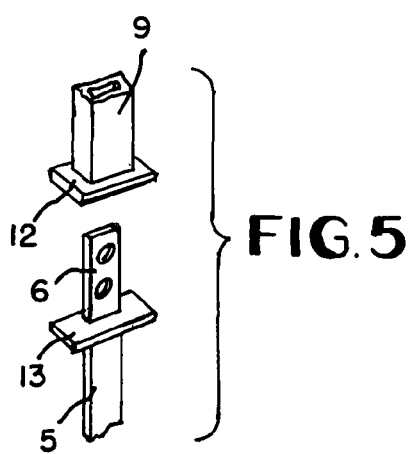

ORTHODONTIC ANCHOR

This is a division of patent application Ser. No. 11/784,566 filed Apr. 9, 2007 now abandoned.

BACKGROUND OF THE INVENTION

It is well known in orthodontics to affix brackets to individual teeth and then fasten an archwire to the brackets such that a tension force is initiated in the desired direction between individual teeth. The resilience of the archwire ultimately results in the desired dentition. Oftentimes the anchor teeth, such as molars, tend to be displaced in an undesirable fashion due to reverse tension forces occurring during orthodontic treatment.

By anchoring an orthodontic appliance to the bone of the mandible or maxilla in order to apply force to certain teeth, the anchor teeth are alleviated from any movement which permits more efficacious correction of the dentition. In addition, attachment of the anchor to bone allows for the positioning of the anchor at the most desirable location to apply the optimum correcting force.

BRIEF SUMMARY OF THE INVENTION

By this invention, an orthodontic anchor comprises a thin plate secured to the bone by means of screws which are placed through angled apertures formed in the thin plate which facilitates easier placement in the mouth. The emerging end of the plate includes apertures for attachment of orthodontic devices such as springs and the like. In addition, a metal cap is attachable to the free end of the anchor to which various orthodontic devices, such as brackets of various types, may be affixed by any known means such as soldering. Also the length of the anchor between the screw bearing end and the emerging end is round or rectangular for ease of bending and passing through the gingival tissues with little adverse reaction. A first transverse rib is formed on the lower edge of the cap and a second transverse rib is integrally joined to the anchor and an elastic band envelopes both transverse ribs.

BRIEF DESCRIPTION OF THE SEVERAL VIEWS OF THE DRAWINGS

In the drawings:

FIG. 1 is a plan view of the orthodontic anchor according to this invention;

FIG. 2 is a cross-sectional view taken along the line 2-2 in FIG. 1;

FIG. 3 is an exploded view showing the emerging portion of the anchor;

FIG. 4 is a side elevational view showing the emerging portion of the anchor;

FIG. 5 is a view similar to FIG. 3 showing a modification of the anchor;

DETAILED DESCRIPTION OF THE INVENTION

Figure 6:
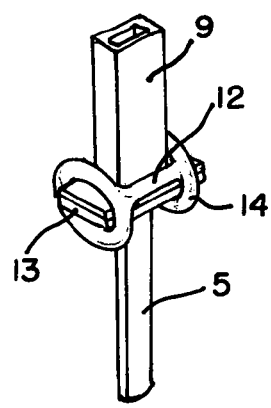
FIG. 6 is the emerging portion of the anchor shown in FIG. 5 in assembled condition.

With reference to the drawings, and in particular FIG. 1, the orthodontic anchor according to this invention is shown and which is generally planar in configuration and including Y-shaped connecting portion 1 having beveled apertures 2, 3 and 4 formed therein. Of course, connecting portion 1 can be of varying shapes besides that shown in FIG. 1 such as an L-shaped configuration. In addition, any number of apertures may be employed and may be disposed at any location on the connecting portion as dictated by the location requirements of the particular orthodontic application.

The anchor shown in FIG. 1 further includes elongated stem 5 with emerging portion or top end 6 formed thereon remote from Y-shape connecting portion 1. Stem 5 is generally round or rectangular so that it can be easily bent for proper placement of connecting portion 1. Apertures 7 and 8 are formed in emerging portion 6, the number and location of which are variable, as desired.

With reference to FIG. 3, hollow quadrilateral cap 9 is shown and includes spring clip 10 which is cut out of one wall of cap 9 with the free end thereof bent inwardly to form tab 11. In practice, emerging portion 6 is inserted into the hollow interior of cap 9 so that spring clip 10 clamps down on emerging portion 6 with tab 11 disposed in either aperture 7 or 8 to effectively lock cap 9 in position.

A modified form of the anchor is shown in FIG. 5 wherein transverse rib 12 is formed on the lower edge of cap 9 with transverse rib 13 integrally joined to the anchor between stem 5 and emerging portion 6. By the utilization of transverse ribs 12 and 13, cap 9 is secured to the anchor by placing cap 9 over emerging portion 6 such that transverse ribs 12 and 13 are disposed in a face contacting relationship, as shown in FIG. 6. Then, cap 9 is secured firmly in place by means of placing enveloping elastic band 14 around transverse ribs 12 and 13, as shown in FIG. 6. More specifically, elastic band 14 includes a pair of spaced circular elements interconnected by at least one attachment rib. The circular elements disposed parallel to each other envelop the ends of transverse ribs 12 and 13 which protrude horizontally outward of the anchor. Other securing means such as a wire and the like can be substituted for elastic band 14.

In orthodontic practice, by this invention, initially it is necessary to attach Y-shaped connecting portion 1 to the mandible or maxilla by means of screws 15 and 16 which are inserted through respective apertures 2, 3 or 4 as determined by the clinician so as to attach the anchor to bone. According to a feature of this invention and as shown in FIG. 2, apertures 2, 3 and 4 are angled with respect to the planar configuration of the anchor. Also, the openings of apertures 2, 3 and 4 are beveled so that the heads of screws 15 and 16 may seat without protruding from the anchor. Positioning of the screws at an angle makes intra-oral placement of the screws easier by facilitating placing screws 15 and 16 into bone from outside of the mouth.

Figure 7:
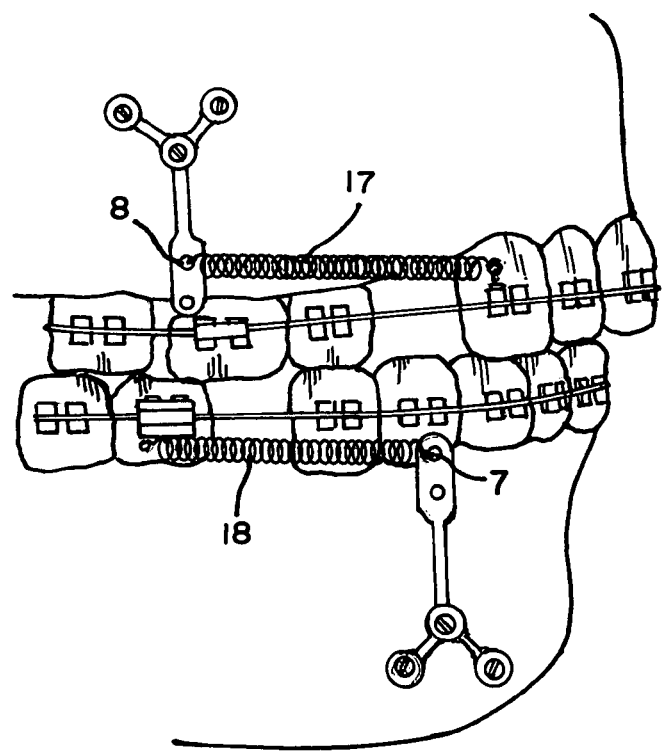
FIG. 7 depicts the anchor affixed in position to both the mandible and maxilla.

FIG. 7 shows the orthodontic anchor, according to this invention, fixed to both the mandible and maxilla with springs 17 and 18 attached to the respective aperture 7 or 8 of emerging portion 6. The opposite ends of springs 17 and 18, respectively, are attached to an orthodontic bracket or other appropriate orthodontic appliance, as is well known, to provide traction on the dentition in either a forward or rearward direction, as desired.

For the purpose of marketing the orthodontic anchor, according to the invention, the anchor together with screws and a screwdriver can be sold in a sterile package. Of course, this type of package is convenient and time saving for the clinician.

Therefore, by this invention, an orthodontic anchor is provided which is fastened to the mandible and/or maxilla to provide tension to the teeth in multiple directions without relying on one end of the orthodontic appliance being attached to teeth other than those being moved.

The invention claimed is:

1. An orthodontic anchor being of planar configuration comprising a connecting portion, an elongated stem secured to said connecting portion, an emerging portion secured to said stem remote from said connecting portion, wherein said stem and said emerging portion are coplanar at least one aperture formed in said connecting portion, a quadrilateral hollow cap fully enveloping said emerging portion, a first transverse rib formed on the lower end of said cap perpendicular to a longitudinal axis of said cap, a second transverse rib integrally affixed to said anchor between said emerging portion and said stem and disposed perpendicular thereto, wherein said first and second transverse ribs are interconnected in flat face contacting relation by a fastener, said fastener comprising an elastic band including a pair of spaced circular elements interconnected by an attachment rib, wherein opposing portions of said first and second transverse ribs extend outwardly beyond said cap in a direction perpendicular to the longitudinal axis of said cap and said circular elements respectively envelop said opposing portions.

2. An orthodontic anchor according to claim 1 wherein said aperture formed in said connecting portion is disposed at an angle less than 90 degrees with respect to said planar anchor.

3. An orthodontic anchor according to claim 1 wherein said circular elements are disposed parallel to each other.

\* \* \* \* \*